United States Patent [19]
Daneshvar

[11] Patent Number: 5,376,067
[45] Date of Patent: Dec. 27, 1994

[54] PRESSURE BANDAGES AND DRESSINGS

[76] Inventor: Yousef Daneshvar, Northville, Mich. 48167

[21] Appl. No.: 967,379

[22] Filed: Oct. 28, 1992

[51] Int. Cl.5 .............................................. A61B 17/12
[52] U.S. Cl. ...................................... 602/58; 602/13; 606/202
[58] Field of Search ...................... 606/112, 201–204; 128/118.1; 602/13, 47, 58, 59

[56] References Cited

U.S. PATENT DOCUMENTS

| | | | |
|---|---|---|---|
| 2,493,406 | 1/1950 | Hicks | 128/118.1 X |
| 3,171,410 | 3/1965 | Towle et al. | 128/118.1 X |
| 3,556,096 | 1/1971 | Fuller | 602/58 X |
| 3,659,609 | 5/1972 | Arouete | 606/202 |
| 4,135,503 | 1/1979 | Romano | 128/118.1 X |
| 4,622,957 | 11/1986 | Curlee | 128/118.1 |
| 4,917,112 | 4/1990 | Kalt | 602/58 |
| 4,972,829 | 11/1990 | Knerr | 602/47 X |
| 5,170,781 | 12/1992 | Loomis | 128/118.1 |

FOREIGN PATENT DOCUMENTS

| | | | |
|---|---|---|---|
| 117714 | 9/1984 | European Pat. Off. | 602/58 |
| 910340 | 6/1946 | France | 128/118.1 |
| 821824 | 11/1951 | Germany | 128/118.1 |
| 45062 | 7/1908 | Switzerland | 128/118.1 |
| 4383 | 10/1880 | United Kingdom | 128/118.1 |
| 9011744 | 10/1990 | WIPO | 606/202 |

*Primary Examiner*—Michael H. Thaler

[57] ABSTRACT

Various embodiments of pressure bandages use a balloon for applying pressure to a wound through a pad. A cover that is attached to the body by any of several different means holds the balloon against the body, and it contains an open space, or window, providing access to the wound area for wound inspection, pad replacement, observation of bleeding, etc. The window can be closed by a door.

8 Claims, 13 Drawing Sheets

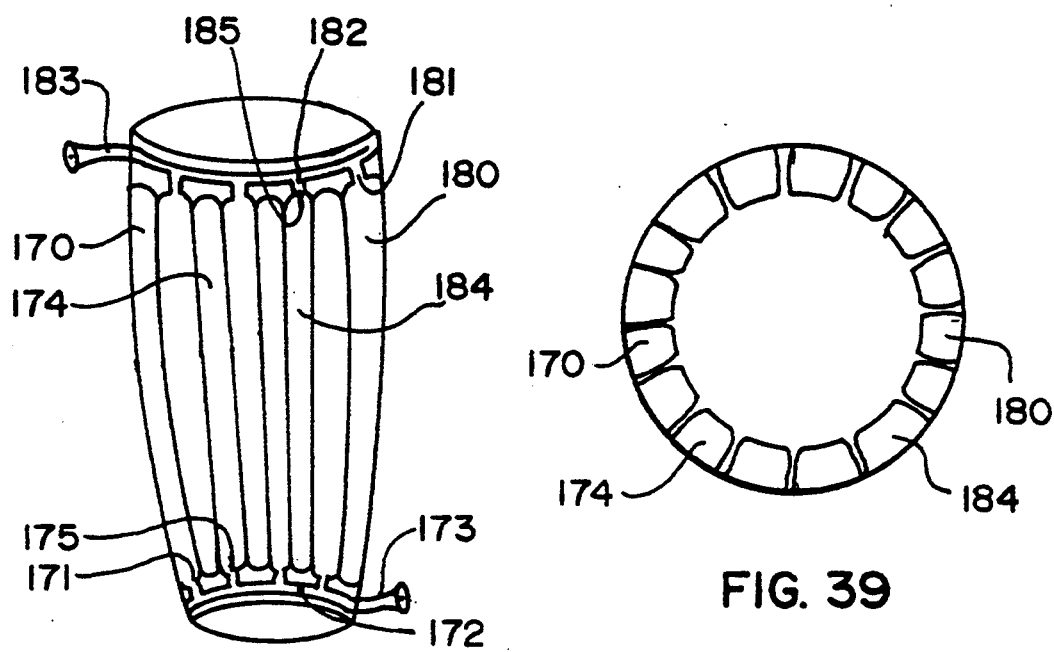
FIG. 38
FIG. 39
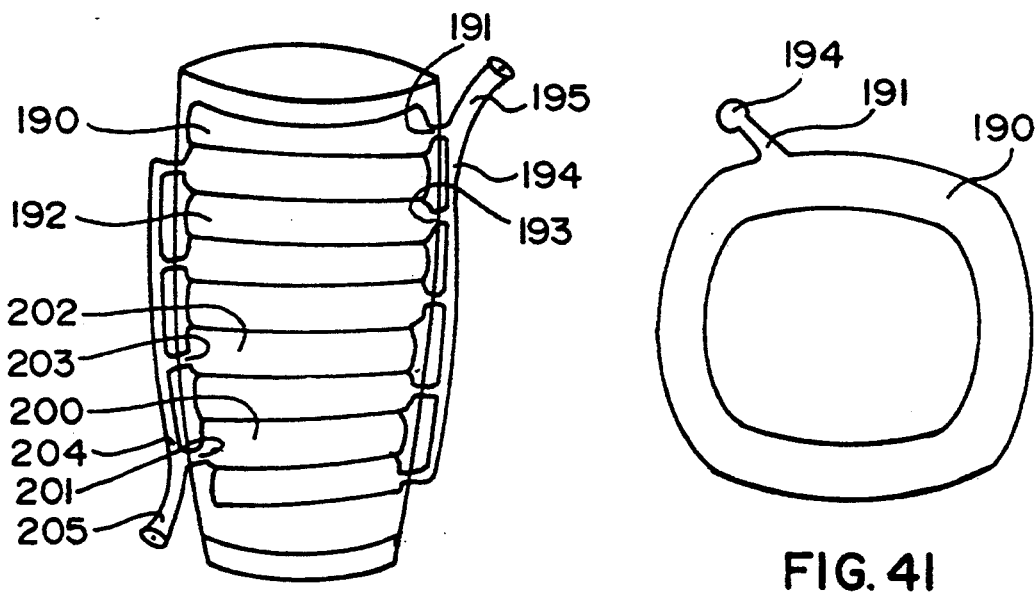
FIG. 40
FIG. 41

PRESSURE BANDAGES AND DRESSINGS

INCORPORATION BY REFERENCE

The disclosures of my pending patent applications Ser. No. 07/800,085 Filed Nov. 29, 1991 and Ser. No. 07/856,087 Filed Mar. 19, 1992 are incorporated by reference as if fully set forth herein.

BACKGROUND

The invention arises because of difficulties I noticed in dressing many of my patients. In many cases we had to spend time and effort to prevent bleeding after certain procedures when a vessel was poked, or a part of a body was cut and operated on and had to be dressed in order for the bleeding to stop. The time that a physician and nurses spends to prevent bleeding using present, and often poorly effective, methods made me think about a better way to do the job. I am glad to say that I believe I have the answer. I have previously asked for patent in my pending allowed application Ser. No. 07/800,085. The present invention would be using the same idea in different places and ways for more expanded use. Basically, this invention introduces the use of pressurized air inside a balloon to be used for dressing the cut area and preventing, decreasing, and controlling the bleeding in different circumstances (especially after surgeries); also to diminish swelling, and to promote ease of mind and good feeling of patients after many surgeries and cases. The problems I have seen with known dressing of a surgical wound have made me present new ideas system after surgeries to help the wound be dressed and the site to be protected from bleeding. In such cases, the balloon will be situated over the bleeding area and over a hydrophilic dressing such as sterile gauze, which may cover the surface of the balloons and be part of the balloon's structure. The balloon will be held in place by various methods such as taping, strapping, wrapping, etc.

SUMMARY OF THE INVENTION

This invention combines pressure applied by a balloon with a dressing to prevent bleeding after procedures, such as removal of subclavian or arterial lines, hip surgery, insertion of pacemakers, herniorrhaphy, etc., where there is need for a pressure bandage to prevent bleeding. Modification can be used to protect the post-surgical wound from being disrupted due to pressure from inside the body. This method uses a balloon that matches the size of the area. When inflated, it will press over a sterile hydrophilic absorbent material, such as cotton (gauze) or other synthetic materials to prevent bleeding. The gauze is to absorb blood and secretions, and the balloon is to press the wound with use of appropriate pressure to prevent bleeding. It is important to notice that pressure by itself will prevent or decrease the oozing of the blood and secretions from the body and the body surface. This can be important in certain circumstances such as burned tissue that is the source of significant oozing or serum and fluids. The balloon can be kept in place with the use of adhesive tapes, or by a wrap or straps, whichever is desired to be used. The straps and wraps will have the great advantage of avoiding the need for removing the adhesive tape and applying it over again. This will prevent the pain of removing the adhesive tape as well as allowing the wound to be checked easily and more frequently. The use of such a pressurized method may be quite useful in the application of certain medications on the skin too.

BRIEF DESCRIPTION OF THE DRAWINGS

FIG. 38 is a front elevation view of a fourteenth embodiment.
FIG. 39 is an end view of FIG. 38.
FIG. 40 is a front elevation view of a fifteenth embodiment.
FIG. 41 is an end view of FIG. 40.

DETAILED DESCRIPTION OF DRAWINGS

Figure 1:
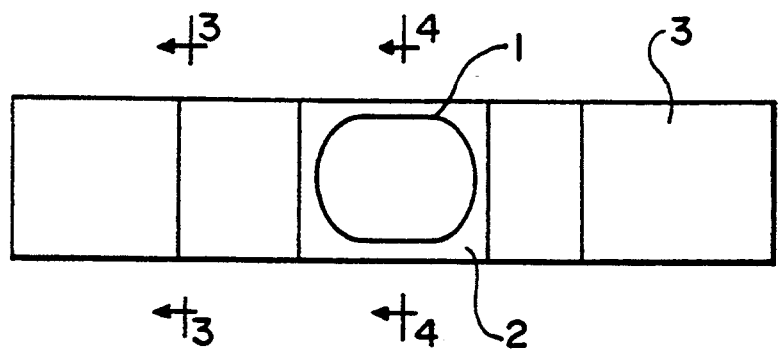
FIG. 1 is a plan view of a first embodiment.
Figure 2:
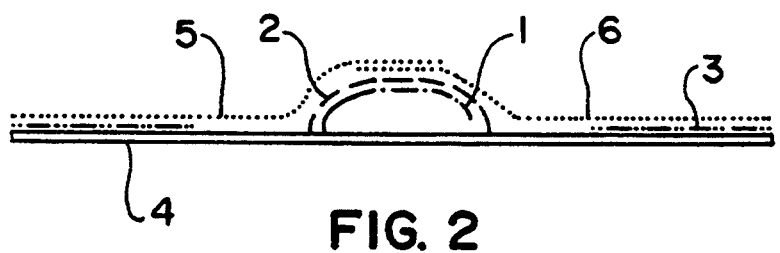
FIG. 2 is an elevation view of FIG. 1.
Figure 3:
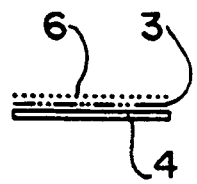
FIGS. 3 and 4 are cross sectional views at lines 3—3 and 4—4 in FIG. 1.
Figure 4:
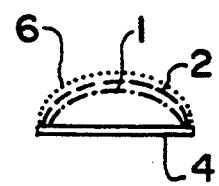
Figure 5:
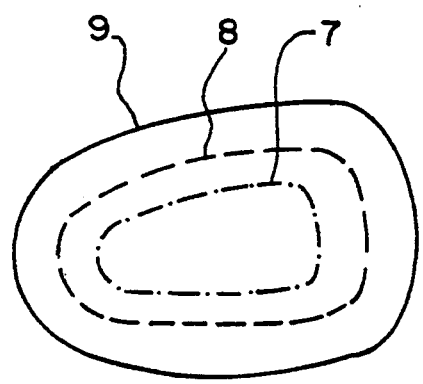
FIG. 5 is a plan view of a second embodiment.
Figure 6:
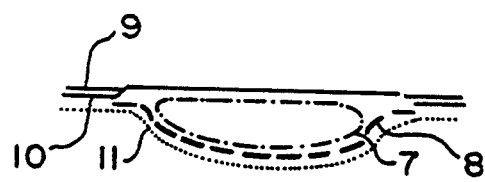
FIG. 6 is a front elevation view of FIG. 5.
Figure 7:
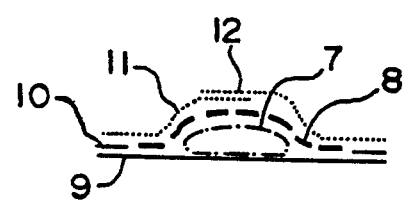
FIG. 7 is an end elevation view of FIG. 5.

FIGS. 1-4 show a pressure bandage which is small so that it can be used in venipuncture and small skin surgeries such as biopsies, mole removal, superficial lacerations, etc. It comprises a balloon 1, and absorbing pad of sterile gauze 2, areas of adhesive Film 3, a supporting base 4, a cover 5, and a cover 6. Balloon 1 in the center is covered by pad 2. At the ends, supporting base 4 is covered by adhesive film 3. Covers 5 and 6 are plastic, which covers the adhesive film as well as the surface of the whole unit to prevent contamination. One end of cover 5 overlaps an end of cover 6 for further protection. Supporting base 4 is a layer of rather non-stretchable soft plastic.

Figure 8:
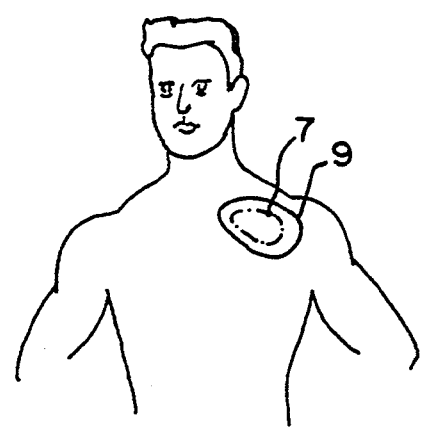
FIG. 8 is a view showing use of the FIG. 5 embodiment.

FIGS. 5-8 show a pressure bandage made to be used in the subclavian area for prevention of bleeding after the removal of a Swan-Ganz catheter and temporary pacemakers. It can also be used with some modification after inserting permanent pacemakers. The shape is different to match the anatomy of the area, a narrow end toward the center of the chest, and a wider end toward the shoulder. The bandage comprises a balloon 7, a sterile absorbing pad of gauze 8, a supporting back part 9, adhesive film 10, a cover 11, and a cover 12. Balloon 7 is in the center and is covered by pad 8. The rim of supporting back part 9 is covered by adhesive film 10. Covers 11 and 12 cover adhesive film 10 as well as the surface of the whole unit to prevent contamination. FIG. 8 shows a patient with this unit applied to the subclavian area.

Figure 9:
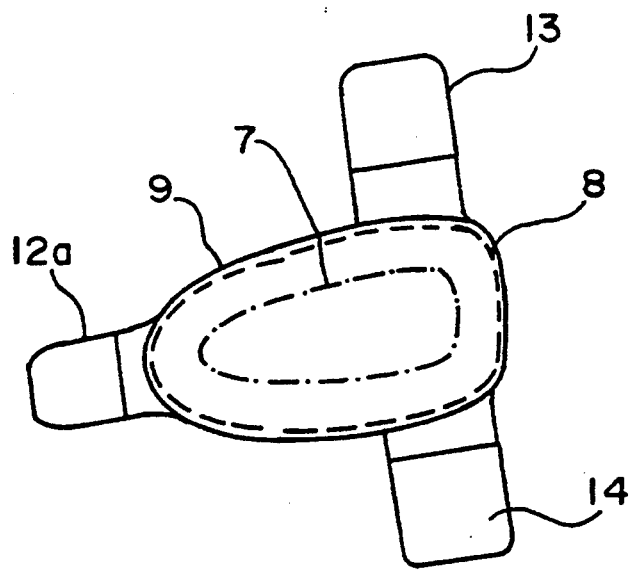
FIGS. 9, 10, and 11 correspond to FIGS. 5, 6, and 8, but show a modification so that they form a third embodiment.
Figure 10:
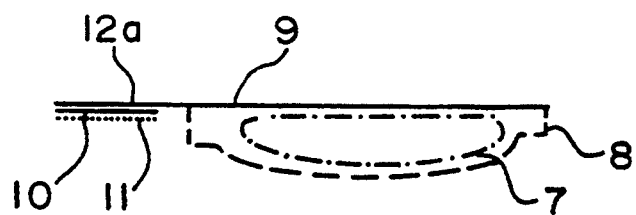
Figure 11:
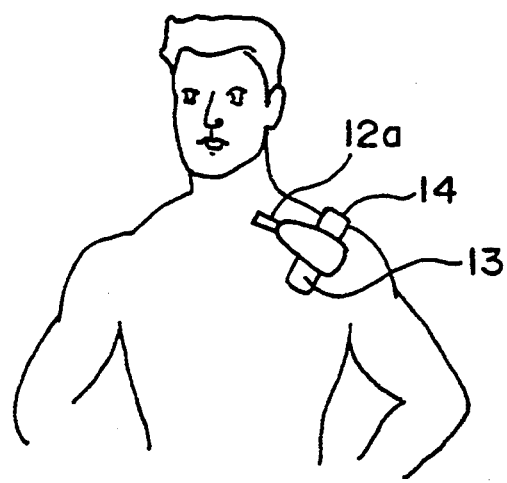

FIGS. 9-11 show a pressure bandage similar to the previous unit. The unit of FIGS. 9-11 has three extensions, or tongues, 12a, 13 and 14, that are to have adhesive film on their surface to allow the unit to be stuck to the skin as shown in FIG. 11. The plastic covers 11 covers the adhesive film.

Figure 12:
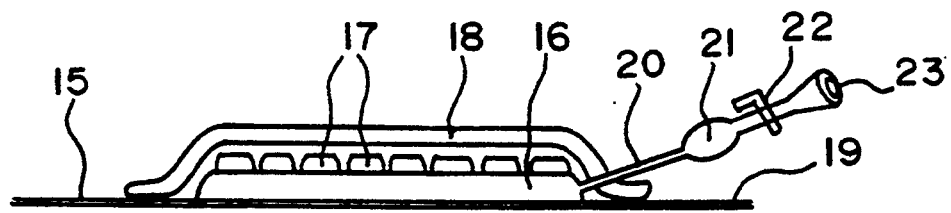
FIG. 12 is a front elevation view of a fourth embodiment.
Figure 13:
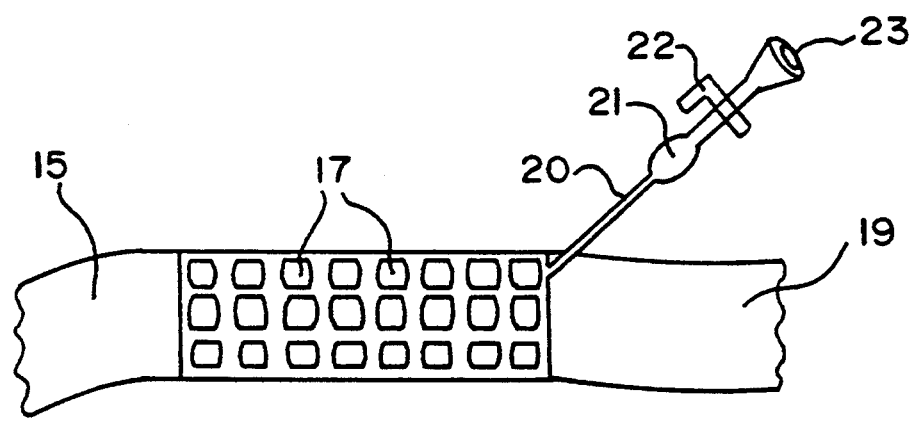
FIG. 13 is a plan view of FIG. 12.
Figure 14:
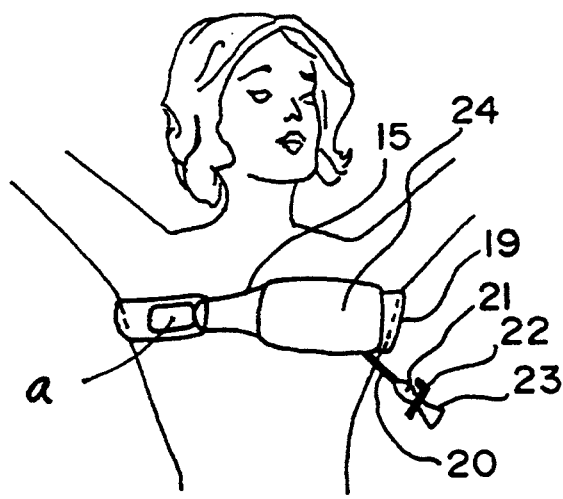
FIG. 14 shows use of the FIG. 12 embodiment.

FIGS. 12-14 show a unit that has two groups of balloons: one large, flat balloon 16 over which is a layer of mosaics of smaller balloons 17. Balloon 16 has a connection to an inflation port 23 through a valve 22 that can be closed. This connection contains a small balloon 21 that will allow the pressure of 16 balloon to be estimated. The layer of mosaics of balloons 17 is disposed over, but is separate from, the balloon 16. The ends of supporting system 24 for this unit are like wide straps 15 and 19 that come together to hold it in place around the area of use. The bottom of balloon 16 is disposed against a central area of supporting system 24.

FIG. 14 shows use of the unit after mastectomy of the left breast. The strap goes around the chest as shown with the place where the ends are stuck to each other, being a. Supporting system 24 covers the balloon and the whole unit. Straps 19 is locked at a to the end of strap 15 by the use of a Velcro TM end that goes through a snap at the end of strap 15 to make a U-turn and then come and stick to its own matching surface.

Figure 15:
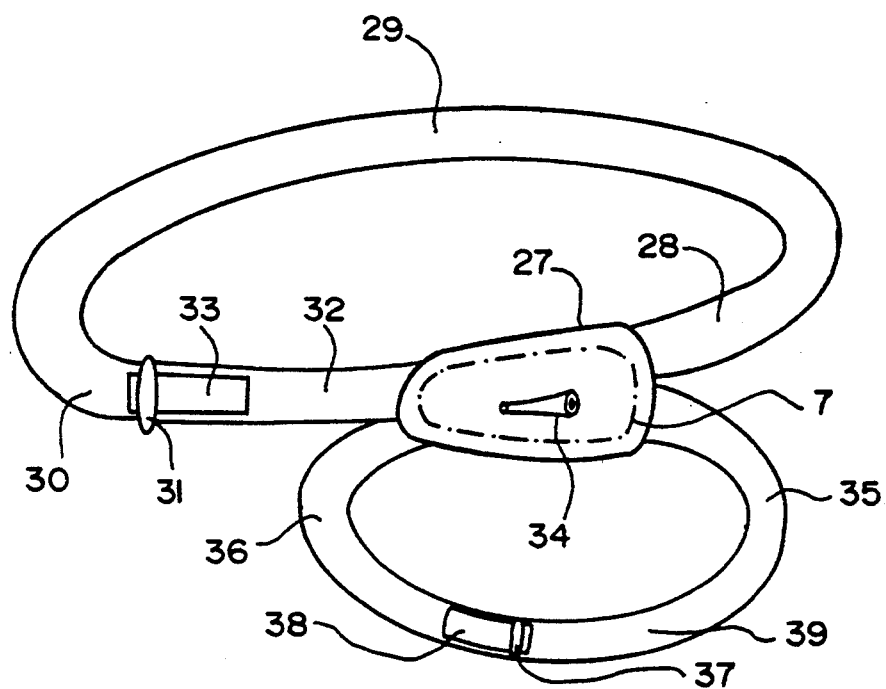
FIG. 15 is a plan view of a fifth embodiment.
Figure 16:
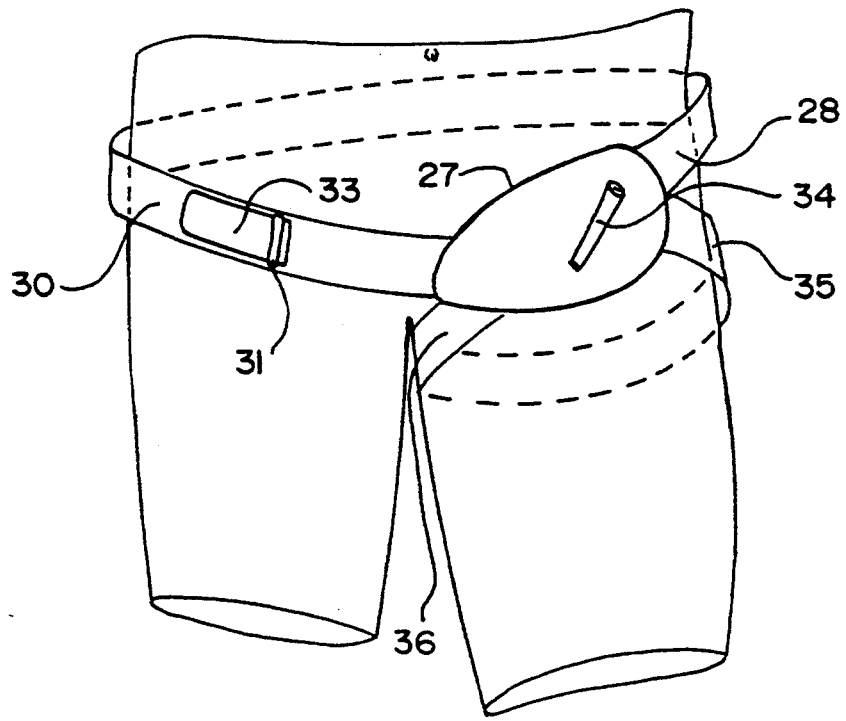
FIG. 16 shows use of the FIG. 15 embodiment.

FIGS. 15 and 16 show a unit for covering the wound after an inguinal hernia operation. Balloon 7 has inflation port 34 in the center, and two straps: a longer one 28-29-30-32 that goes around the waist, and a shorter one 35-39-36 that is to encircle the thigh. These straps will be tightened by the use of a Velcro TM system (not shown in detail in the Fig.) that is made at one end of each strap and will allow one end to go through a snap and make a U-turn, then come and stick to its own back, 31 and 33 being for the waist strap, and 37 and 38 being for the thigh strap. In FIG. 16, the unit is over the operated area in the groin area. The unit is held in place with the use of the two straps.

Figure 17:
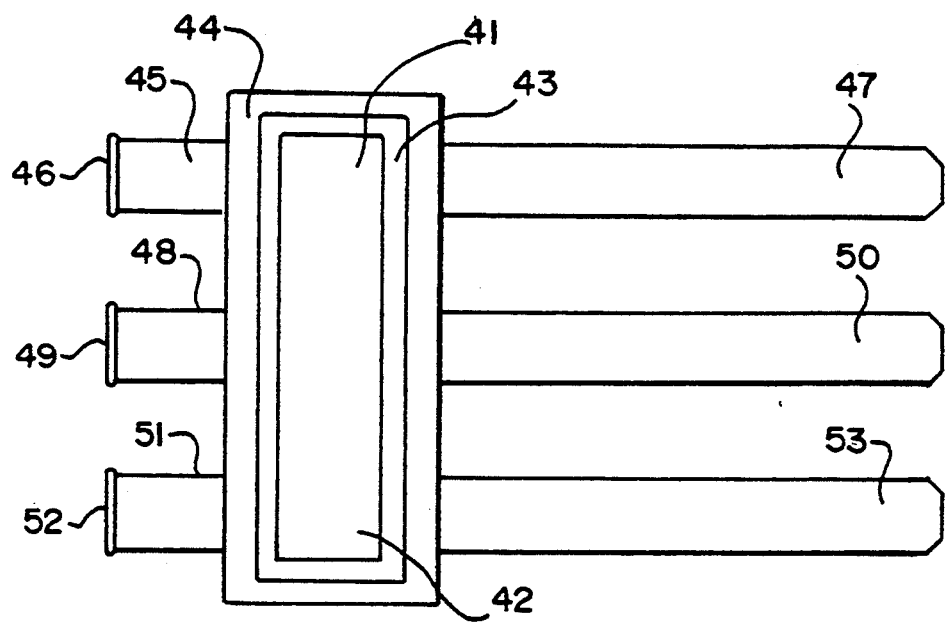
FIG. 17 is a plan view of a sixth embodiment.
Figure 18:
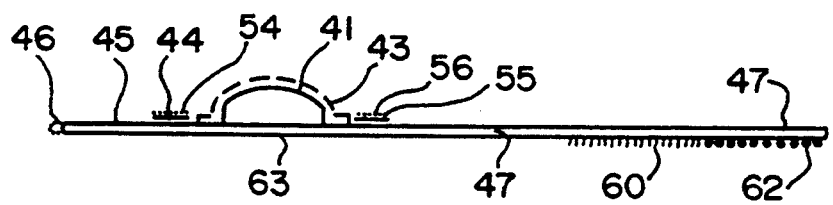
FIG. 18 is a front elevation view of FIG. 17.
Figure 19:
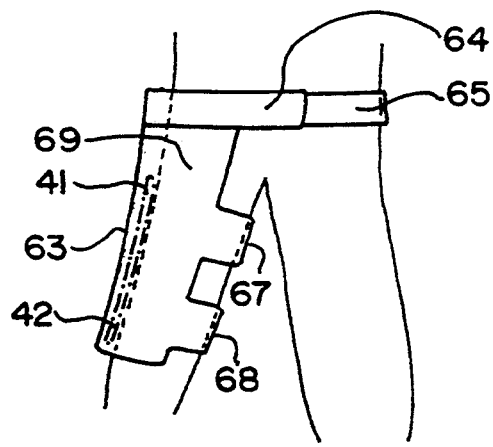
FIG. 19 is a view showing use of the FIG. 17 embodiment.

FIGS. 17-19 show a unit for use after a hip operation.

FIG. 17 shows the unit spread on a flat surface or a table. A similar unit with modification can be used after open-heart surgery. A balloon 41, 42 in the center is covered with absorbing layers of gauze 43, surrounded by edges of the supportive system 44 which may be covered by adhesive film. The straps on the left side of FIG. 17 and 18 are 45, 48 and 51, and each ends with a piece 46, 49, 52, respectively, that will allow the end of the other matching strap from the other side of the unit 47, 50 and 53 to come and go through it to make a U-turn and then, with the use of Velcro TM patches in its own end (ends of straps 47, 50 and 53) to secure the position of the unit. The balloon is to left of center. The adhesive film is shown by 44 and 55, and the plastic which covers the adhesive film by 54 and 56. The support system is 63. FIG. 18 shows strap 47 with its lower surface covered by a Velcro TM patch, the rough surface shown by 60, and the softer one by 62.

FIG. 19 is the general appearance of the unit when it is in place on the right side of the right thigh. An upper strap 64, 65 goes around the waist of the person. The middle 67 and the lower 68 straps go around the thigh of the person to secure it in place. No. 69 shows the front part of the support system.

Figure 20:
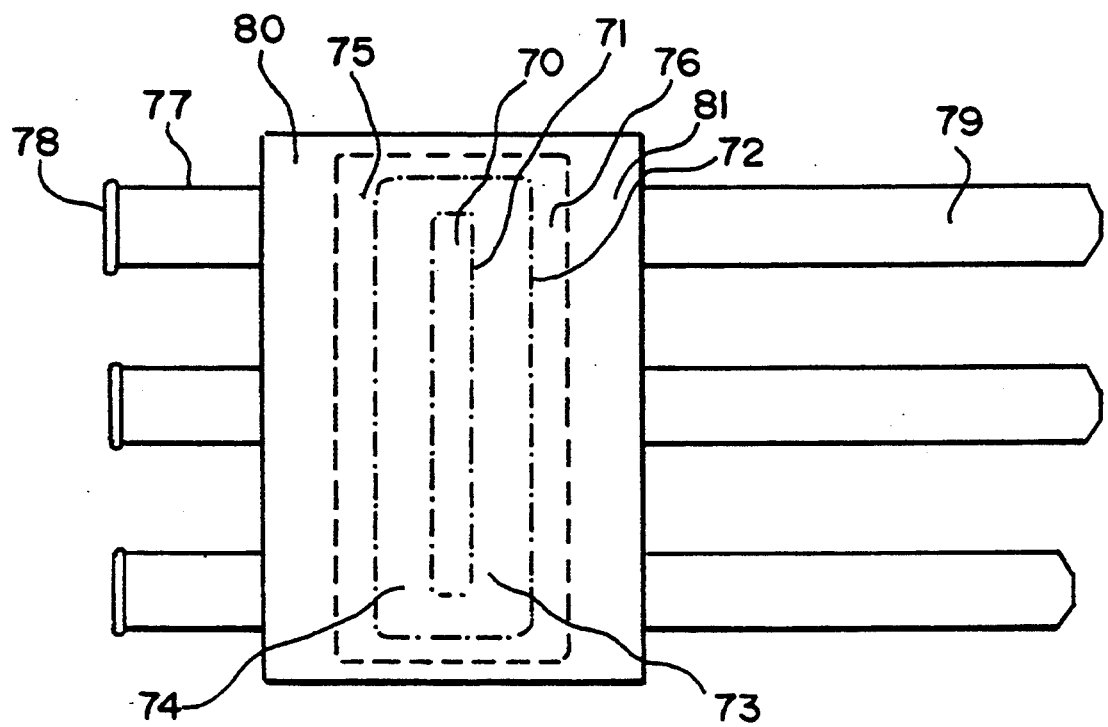
FIG. 20 is a plan view of a seventh embodiment.
Figure 21:
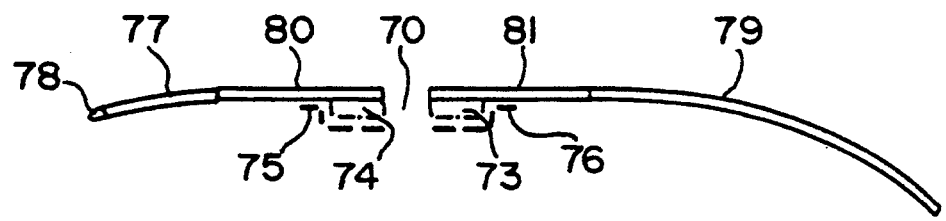
FIG. 21 is a front elevation view of FIG. 20.

FIGS. 20 and 21 show another unit for covering wounds similar to the one after a hip operation. This unit has a window in its center to allow selective access to the site of the incision. The balloon has inside 71 and outside 72 borders. The right side is 73 and the left side is 74. And the balloon encircles an open window 70 in the center. The outside border of a covering and absorbing layer of gauze is shown at 75 and 76. The rim of a supportive system is 80 on the left and 81 on the right side, and extends all around. This area may have adhesive film. Straps 77 and 79 that will encircle the thigh to hold the unit are shown on the sides. (Only the upper pair are numbered to avoid crowding the figure.) They are very similar to the straps shown in the previous unit.

Figure 22:
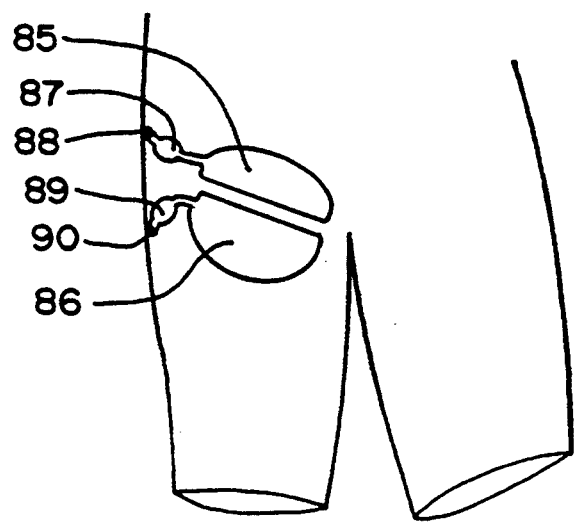
FIG. 22 is a plan view showing usage of an eighth embodiment.
Figure 23:
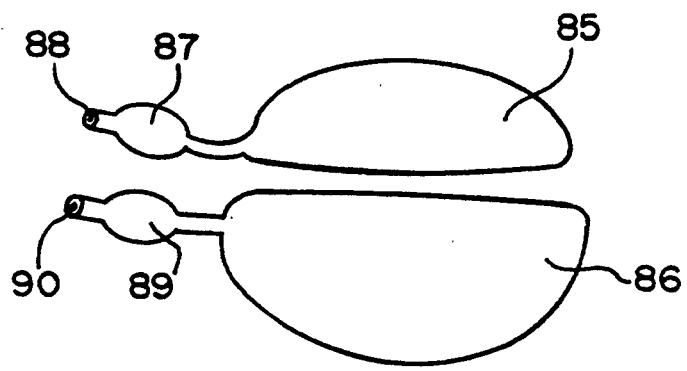
FIG. 23 is an enlarged plan view of the eighth embodiment.
Figure 24:
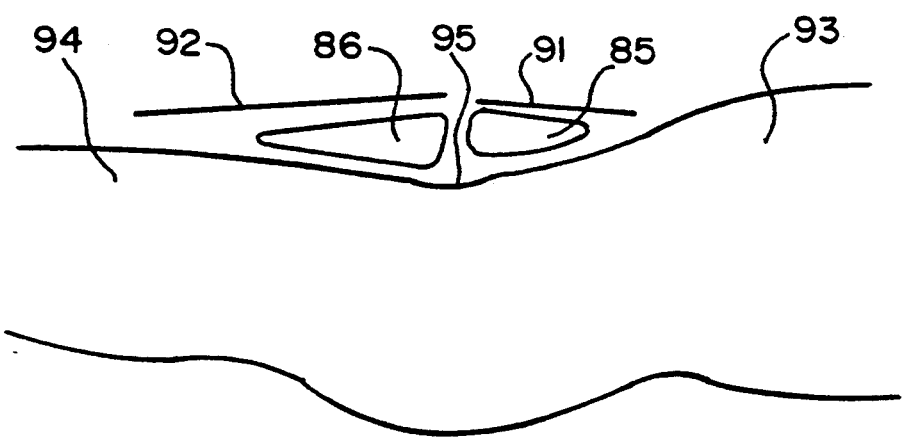
FIG. 24 is a side elevation view showing further detail of usage of the eighth embodiment.

FIGS. 22-24 show a unit with double balloons to be used in the groin after cardiac catheterization and angioplasty, and similar interventions in the groin vessels. FIG. 22 is the general appearance of the unit for preventing and controlling bleeding in the groin area after intervention and angioplasty. Here, the unit is placed in the right groin of the patient, which in practice is mostly used. It comprises two balloons: one, 85, that is placed on the upper part of the groin and lower abdomen over where the big vessels were intervened; another balloon 86 that is on the lower part of the groin and upper thigh, the area where the femoral artery and veins are located. This combination will provide double protection for preventing and controlling the bleeding, which I believe we need at times when hematoma and bleeding occur, both in the groin and lower abdomen, based on cases that I have witnessed. This combination has smaller balloons 87 and 89 located in the course of the inflation tube for estimating the pressure inside the bigger balloons. These balloons may be connected by a smaller tube to the hose of the main balloon, although a manometer can be used to measure the pressure, and an alarm can be hooked up for further security. FIG. 24 shows the crosscut view of the unit of FIGS. 22-23 placed in position on a patient lying on a table of a catheterization lab. The patient's head is on the right, and the feet on the left. Here, the position of the upper balloon 85 and the lower one 86 is illustrated compared to the inguinal line 95. The wraps are also shown: the upper wrap 91, which stands over the balloon 85, and the lower wrap 92, which stands over the lower balloon 86.

Figure 25:
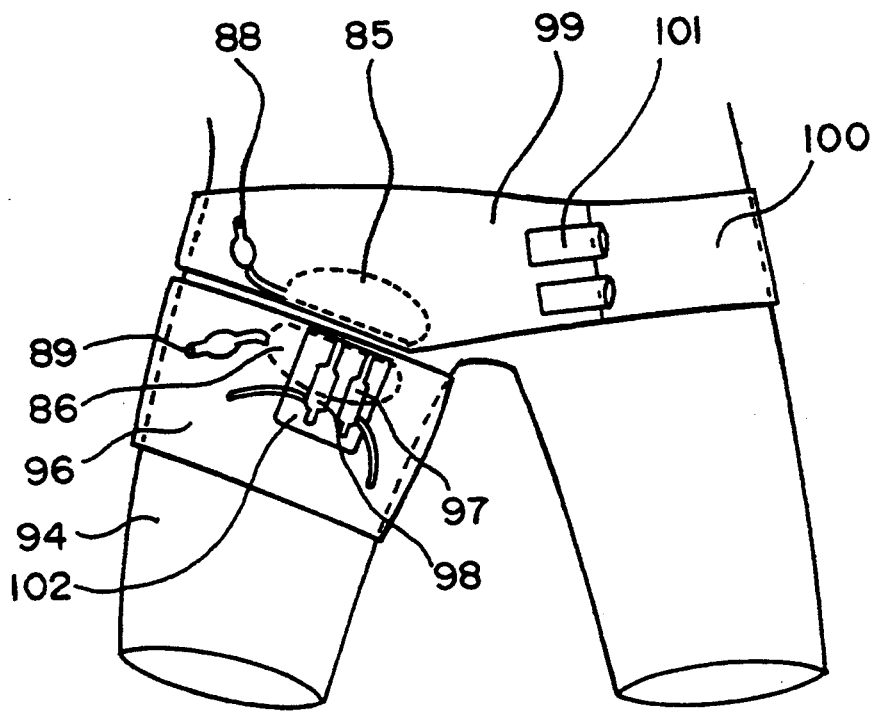
FIG. 25 is plan view similar to FIG. 22 showing further usage detail.
Figure 26:
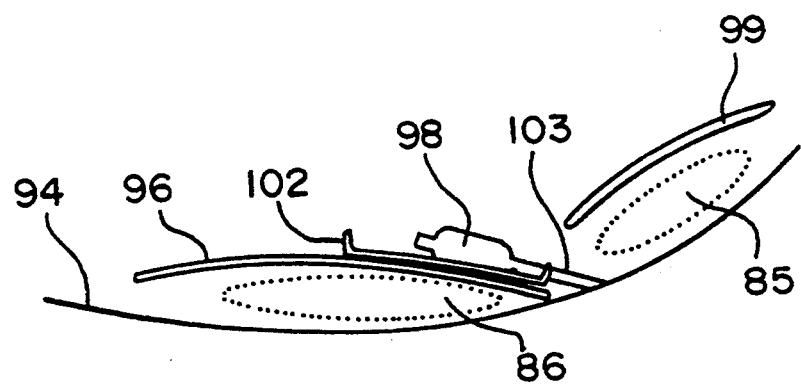
FIG. 26 is a side elevation view of FIG. 25.

FIGS. 25 and 26 show the general appearance of a unit similar to the one shown in FIG. 24, except that here the unit is in place and covered by wraps. The wrap over the lower part has a tray 102 that has a matching cradle that will allow the arterial and venous sheaths to be placed and be held securely in place by another wrap going over them (not shown in this picture). In FIG. 25, the upper balloon 85 is located in the lower part of the abdomen and is supported by the wrap 99, whose end 100 comes from the left side, and is held with two small belts of which the upper one is marked 101. This is similar to the one mentioned above, and is made from Velcro TM cover straps. The lower balloon 86 is supported by the wrap 96 which goes around the thigh. The ends of this wrap will also be held tightly together with the use of straps not shown here. The main bodies of the arterial 98 and venous 97 sheaths are placed in matching cradles of tray 102 made for such placement.

FIG. 26 shows the unit placed on a patient lying on a table. The patient's head is on the right, and the feet on the left. Here, the upper balloon 85 is placed on the lower abdomen, right above the groin line, where the sheaths are inserted in the groin area, and the wrap 99 is supporting it. The lower balloon 86 is in the upper groin, right below the point where the sheaths have entered the groin and are supported by the wrap 96. The tray 102 is in place, and the arterial sheath 98 is in place, with its front tubular end 103 going into the skin.

Figure 27:
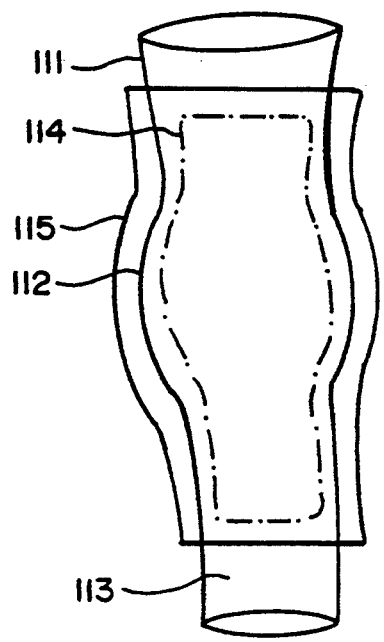
FIG. 27 is a front elevation view of a ninth embodiment.
Figure 28:
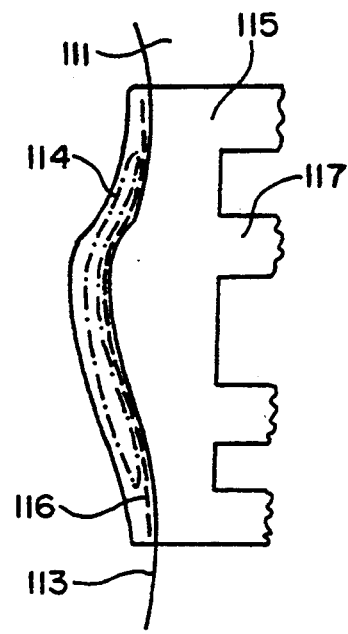
FIG. 28 is a side elevation view of FIG. 27.

FIGS. 27 and 28 show a unit which is used to cover the patient's knee after knee surgery, as well as knee placement. Here, the lower thigh, above the knee, is shown by 111, the right side of the knee by 112, and the upper leg by 113. The balloon is shown in the center. It is held in place over the gauze 116 by the support system 115. The support system has straps that go around the knee, lower thigh, and the upper leg to hold it in place. Only one of these straps is marked here by 117.

Figure 29:
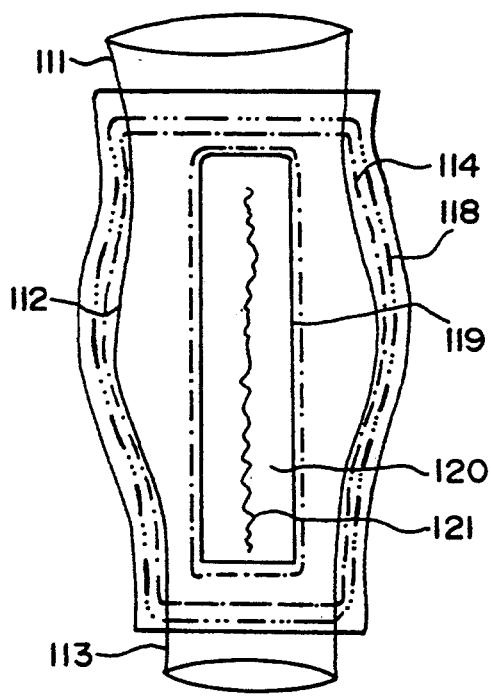
FIG. 29 is a front elevation view of a tenth embodiment.

FIG. 29 shows a unit similar to the one shown in the previous two Figs., except that this unit has a central window that allows the incision of the skin to be seen through. The balloon surrounds this window, and the window is covered by a piece of shaped plastic that will sit over the balloon to give further desired support and shape, and also to hold the knee in position. The central window is shown by 120 with its border 119. The incision site 121 on the skin can be seen through the window. The hard plastic part is marked by 118.

Figure 29A:
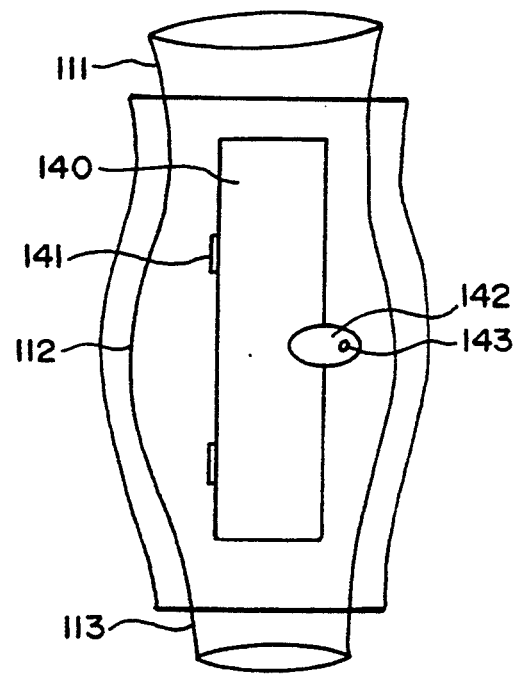
FIG. 29A is a front elevation view of an eleventh embodiment.
Figure 42:
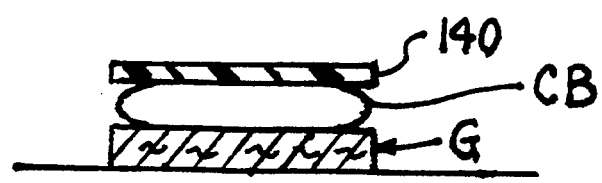
FIG. 42 is a fragmentary transverse cross sectional view through a portion of a modified form of FIG. 29A.

FIG. 29A shows a unit similar to the one shown in the previous Fig., except that a door 140 opens and closes window 120. This door is attached to the plastic by two hinges 141, and the window can be opened for the insertion of a piece of matching gauze. After the new gauze has been inserted, the door can be closed and kept tight with the use of a small latch 142 that can be rotated to hold the door closed. A small screw or pole will hold the latch on the surface of the plastic to allow it to be rotated. The door can be made from clear plastic to give the chance for observing the inside. A clear balloon can be made inside the door to allow the control of pressure on the gauze. This balloon can be permanently or temporarily sealed. FIG. 42 shows such a clear balloon CB between door 140 and the gauze G, an example of which gauze will be described in connection with FIGS. 35–37.

Figure 30:
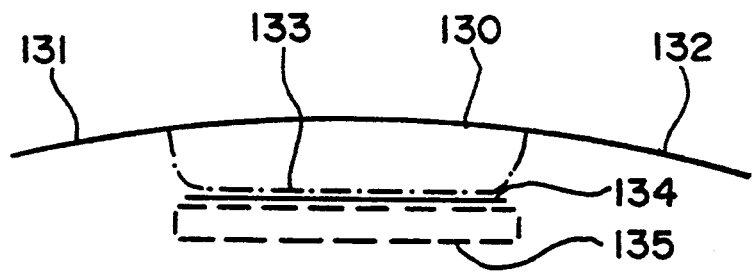
FIG. 30 is a front elevation view of a twelfth embodiment.
Figure 31:
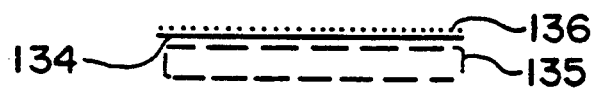
FIG. 31 is a front elevation view of a portion of FIG. 30 shown by itself before its incorporation into the twelfth embodiment.
Figure 32:
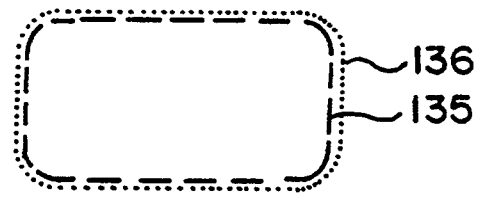
FIG. 32 is a plan view of FIG. 31.

FIGS. 30–32 show a unit that has a balloon over a supporting wrap or strap, and on this balloon a piece of gauze is stuck by the use of adhesive film. The back support (strap or wrap) is shown by 130 with its end pieces by 131 and 132. The balloon is shown by 133, the adhesive film by 134, and the pad of gauze by 135. The pad of gauze 135 is covered by the adhesive film 134, which is covered by a plastic cover shown by 136.

Figures 33, 34:
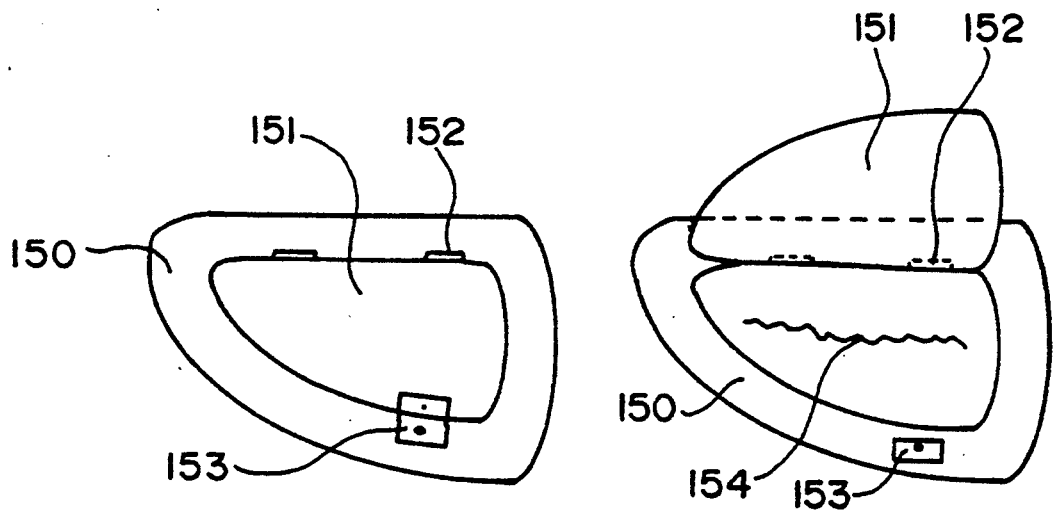
FIGS. 33 and 34 are plan views of a thirteenth embodiment showing two different positions.

FIGS. 33 and 34 show a unit similar to the one in FIGS. 15 and 16, which is to be used after hernia operations, except that here the unit has a cover over a window that will allow easy inspection, as well as dressing, as explained in the application. No. 150 is the outside rim of the support system, and a central cover 151 is connected to the rim by hinges 152. A snap 153 is also shown, and when it is released, the cover can be opened. FIG. 34 shows central cover 151 open and the incision 154 can be seen.

Figure 35:
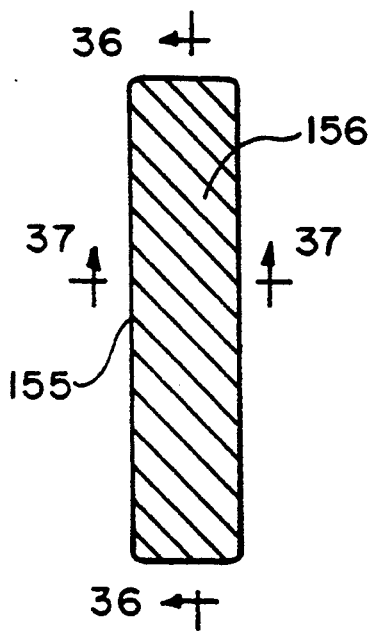
FIG. 35 is a plan view of an accessory for a previous embodiment.
Figure 36:
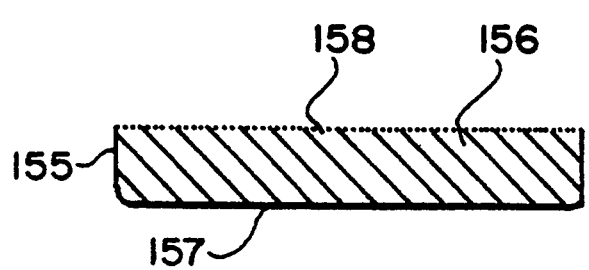
FIGS. 36 and 37 are cross sections through FIG. 35 in the directions of arrows 36—36 and 37—37.
Figure 37:
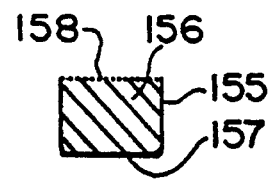

FIGS. 35–37 show a long pad of gauze that is designed to be used with a unit similar to the one shown in FIGS. 29 and 29A. This unit consists of a central pad of gauze shown by 156, surrounded with a plastic wall 155. This is to prevent the secretions absorbed by the gauze from diffusing and reaching the inside wall of the balloon. This will be packed individually. The surface of the pad is 158, and the plastic wall is at 157 and 155.

FIGS. 38 and 39 show a unit that is to be used under a leg cast. This unit has two groups of balloons that are parallel to each other and are connected to each other alternatively. For example, the balloons 170 and 174 are connected to an inflation port 173, with small connections 171 and 175, that connect to a horizontal tube 172, that goes to the inflation port 173. Likewise, the balloons 180 and 184 are connected to an inflation port 183 with small connections 181 and 185 that connect to a horizontal tube 182, that goes to the inflation port 183. This will allow only one group of these balloons to be inflated without having a connection to the other group, and vice versa. The supporting system will be around the balloons and the inside cover inside the balloons. The groups of the balloons are next to each other, and they will hold the leg inside themselves safely. It will give the chance to imagine how deflation of one group of the balloons will not cause total collapse of the whole unit.

FIGS. 40 and 41 show a unit similar to the ones of FIGS. 38 and 39; except, here, the two groups of balloons that are parallel to each other are horizontally placed. It also shows that these balloons are connected to each other alternatively. In FIG. 40, the balloons 190 and 192 are connected to an inflation port 195, with small connections 191 and 193 that connect to a vertical tube 194, that goes to inflation port 195. Likewise, the balloons 200 and 202 are connected to an inflation port 205 with small connections 201 and 203 that connect to a vertical tube 204 that goes to inflation port 205. This will allow only one group of these balloons to be inflated without having a connection to the other group, and vice versa. The supporting system will be around the balloon and the inside cover inside the balloons.

DETAILED DESCRIPTION

This invention is based on using pressure applied by a balloon over certain places that either are bleeding or need to be pressed to some degree to prevent bleeding. It will also help to prevent other problems, such as weakening of the abdominal wall due to pressure from inside, and in easier dressing of surgical wounds.

In some ways, this application is about expanding the use of my previous inventions mentioned at the beginning. In this application, I introduce the use of a similar unit made from a balloon or balloons held in place with the use of adhesive tapes, straps, and wraps to serve as a method of preventing bleeding (even in hemophiliacs). It may also be used where oozing of body fluids occur, as well as implementation of some medications through the skin. When modified, this will be a very useful tool for the prevention of bleeding, as well as a new way to allow dressing and supporting the site after many different surgeries.

Known techniques for preventing bleeding use layer of gauze to create a mass that is then taped on. Pressure can be supplied either by hand or sandbags. In my experience, gauze alone is not an appropriate way of applying pressure, and the fact that in many cases I have seen them not work is a reason behind my invention. In many cases that I do in my job quite often, such as removing a Swan-Ganz catheter, either myself, or most of the time a nurse, has to press the place until the bleeding stops. Then, the nurse dresses the place by using gauze and heavy taping to prevent further bleeding. I would like to mention that the time of a nurse is very valuable, and the less it can be used/wasted, the better it will be for the better care of patients. In other cases that I have seen in my hospital, such as after hip surgery, the area is covered with heavy adhesive taping, and the dressing is not changed for many days. I believe this poses many problems that I would address. In practice, we doctors and the nurses have to use the adhesive tapes, but their use poses many problems. Here, I will mention some as follows:

1. The pain of removing tapes is so common that its problem can be called obvious.

2. Irritation and infection occur in the areas where tapes are used.

3. Allergy to certain tapes and adhesive materials are very well known in the medical community.

4. The cost of taping can be high, if they are used very frequently.

From the other side, the use of my invention has the advantage of not only cutting the time of dressing and preventing and stopping bleeding significantly, but also decreasing, if not eliminating, the use of adhesive taping. It will introduce a new way of dressing the skin after many operations and interventions. The prototype and basic unit of this invention is very simple and uses the same principle that was utilized in my previous invention about the use of balloons for the prevention of bleeding. This unit (shown in FIGS. 1–4 herein) is made from a rectangular piece of plastic which is stretch-resistant elastic material with a fabric matrix inside that makes the support system for a balloon. This balloon will be one or combinations of balloons which will have a size of about 1.5 to 2 cm. by 1.5 to 2 cm. (In different models, they will have different sizes and shapes.) This balloon or balloons will be covered by a layer of soft hydrophilic material made from gauze or cotton 2. The balloon is supported by a system which is to hold it in place and allow the pressure to be applied to the desired place; it will be a soft, slightly stretchable matrix of soft plastic 4 that has the shape of a long rectangle. The two ends of this rectangle will have a surface covered by adhesive film 3. This adhesive film will be protected by a thin layer of plastic 5, 6 that are removably adhered to the adhesive film, and when they are removed, the adhesive surface will be exposed. These plastic layers will also play the role of protection for the surface of the face of the unit to keep them clean and sterile. This unit will be individually wrapped sterile and can be used to cover small areas that may bleed, such as after venipuncture, or the removal of small moles or after skin surgeries. The balloon will be located over the bleeding spot to press, and the ends will be stretched and stuck on the skin to continue the small amount of pressure for such jobs. The elasticity of the matrix of the supportive system will help in keeping pressure on the spot.

The other units, with different and larger sizes, can be used in emergencies to provide pressure to the cut areas and prevent bleeding.

The main parts of this unit, in general, consist of a balloon which may be made from one single balloon or combinations of multiple balloons, and will be covered by a layer or pad of gauze, and be held in place by a support system that can be a plastic layer, strap, or a wrap. With some creative modifications, many units can be made to be used in different areas of the body and for many different useful cases.

This basic idea, when modified appropriately, will be very useful in preventing the bleeding after procedures such as removing catheters from an artery or big vein as well as after transcutaneous angioplasty, subclavian lines, arterial lines, after certain surgeries such as hip surgery, insertion of pacemakers, and the other surgeries that need a pressure bandage for prevention of bleeding. So, basically, this method uses a matching balloon that will press over a gauze or its own surface that will be covered by a cover similar to gauze. The gauze is to absorb the blood and secretions when the balloon presses the wound to apply the needed pressure to prevent the bleeding. The balloon can be held in place by different methods as follows:

1. Use of tapes or adhesive tapes to hold the balloon in place. This can be achieved either by:
   a. strips of adhesive tapes.
   b. by a film of adhesive that covers the ends of the support system or the rim of the support system of the balloon. This adhesive film will be covered by a plastic protective cover. This plastic cover is removably stuck over the film of glue and will be removed prior to use.

2. The balloon can be held in place by the use of straps that will be connected to the balloon itself, the structure around the balloon, or covering the balloon. The straps may have a component of elastic in the construction to let a pressure over the balloon to be generated also to allow it to be pulled easily for different purposes.

3. It can be held in place with the use of wraps that will go over the balloon and its cover to hold it in place and press the balloon against the area we are interested in to apply the pressure. These wraps may have a component of elastic in their construction to let a pressure over the balloon to be generated also to allow movement of the unit and easily pulling it away from the side where it is used without having a need to be totally removed or opened.

The straps and wraps will have the great advantage that first they will allow creation of many combinations of shapes to hold the balloon in the places we want with ease, and also their use will eliminate or decrease the need for removing the adhesive tapes and applying them over again. This will prevent the pain of removing the tapes as well as allowing the wound to be checked easily and more frequently. These straps and wraps may have a component of elastic in their construction to allow generation of pressure and also to let the pulling of the unit away from the side for a look at the wound without having a need to be totally removed or opened. This may even give the chance of changing the layer or pad of gauze in some cases without even needing to open the straps or wraps. (I believe this is an important concept.)

The balloons used for such purposes may consist of only one single balloon or they can be made from multiple balloons combined together to prevent collapse of the whole balloon if one of them were perforated. Furthermore, this will give a chance for selective inflation of some balloons for different purposes as well as the use of intermittent or alternative inflation of balloons in order to prevent one particular part of skin to be under pressure all the time. The multiple balloons may be combinations of mosaics of balloons, or it can be one balloon with multiple walls inside to prevent from its total collapse, or series of balloons almost parallel to each other. The multiple balloons can be constructed to be in different levels. Also, their inflation port and combinations of them together will be different as well as their functions. For example, I bring the issue of the balloons to be used under the cast for broken limbs. In those cases, long series of balloons or circular series of balloons can be used with different ports of inflation to allow one series of balloons to be deflated when the other group is inflated to prevent disfigurement and collapse of whole unit.

THE ADVANTAGES OF USE OF THE BALLOONS

The use of the balloons has many great advantages. The balloon will not only press the area, but also has the capacity of assuming the shape of the place and adjusting its own surface to some degree, which I believe is an advantage.

The pressure generated by the balloons, unlike the pressure applied by the sandbag in the groin after cardiac catheterization, is not weight-, gravity-, and position-dependent, and so it gives much more freedom, and patients can be mobilized easily and faster.

The pressure applied by balloons, unlike the pressure by sandbag or pads of gauze, can be modified and measured, and easily adjusted and controlled.

The pressure applied by the balloons will not only prevent bleeding, but it may also decrease the secretions, since the drainage of secretions in the cut area will be less due to the natural effect of the counteracting pressure in the area. This fact may be very importantly considered and used in cases of skin burns and similar circumstances when heavy secretions of the serum and fluids from the injured area occur, causing fluid loss in significant amounts.

Use of the balloons for generating pressure by this method has the advantage of allowing it to be easily measurable, controllable, removable, and applicable, which has a great freedom of its own.

THE WINDOWS AND THEIR FUNCTIONS

This is a revolutionary change that can be used with the new dressing technique I introduce here. This new model (shown in FIGS. 20, 21-29, 29A-33 and 34) will be made from a balloon or combinations of the balloons that will be positioned to stay parallel or around the site of the incision after operations to hold the skin and underlying tissues on the sides of the incision in place as desired. There will be an open window in the center of the balloon that will leave the space over the incision site open so that it can be approached freely, without fear of dismantling the whole unit. The wall of this open window may be made from a thicker plastic to give shape to the walls and also to keep them in shape afterward.

This new technique will give the following unique chances:

1. The wound or incision site can be seen easily through the window, and more frequently, without the need to change the whole dressing. This is a big advantage in that bleeding, infection, and necrosis can be diagnosed and treated earlier.

2. The wound or incision can be wiped and cleaned easily with the use of swabs or cotton balls held by hemostats, without a need for changing the whole dressing; again, a very useful advantage.

3. The wound or incision can be left open to air for some period of time without removing pressure from the sides and displacement or dismantling the whole dressing, as well as bone structure and new implanted parts, etc.

4. The wound or incision may be exposed to heating lamps to gain the benefit of its use in drying the skin and giving heat, and maybe killing germs in the area too.

5. The balloons may be used to give heat or cold by running warm or cold water inside them without affecting the system. Naturally, an electrical heating element may be used for this purpose.

6. A selective, intermittent, and rotating pressure can be applied by use of groups of balloons, which is not easily possible by the routine methods. This will give its own great advantage from preventing a constant pressure to one spot and compromising the circulation.

7. The use of balloons will eliminate the waste of thick layers of dressings and gauze to be used for generation of pressure and holding the wound, when a thin or smaller layer of gauze can be used to cover the balloon.

THE CONSTRUCTION OF THE GAUZE

The absorbing, sterile gauze (FIGS. 30, 31, 32, 35, 36 and 37) are made from sterile, absorbent material commonly used for such purposes. These units will have their own special shapes to match the unit with which they are intended to be used, and they may have a plastic wall around them (except the surface that is to absorb the secretions) in order to keep them in the desired shape. They can be inserted inside the open window in the center of the balloons, and can be exchanged easily by removing the old one and inserting the new gauze instead of the used one. The plastic cover or wall around the sides of the gauze will prevent from contaminating the sides of the balloons with the secretions. The surface of some of these may be premedicated for saving the time of preparation and simplicity.

THE GAUZE WITH COVER OF ADHESIVE

The exchange and use of new pads of gauze can be easily done with the use of balloons. For such uses, a layer of sterile gauze can be made (FIGS. 30, 31 and 32) with a back surface covered by plastic that has adhesive film on it. This adhesive film will be protected by a thin layer of plastic that will be removably adhered to the layer of film. Then, at the time of use, the cover will be removed and the layer of gauze will be stuck to the surface of the balloon to be positioned in place. This will make the job of exchanging the dressing easier and simpler. Naturally, the thickness of the gauze, as well as its size and shape, will be different to allow a right choice for the wound for which it is intended to be used, considering the amount of secretions, etc. These can be sterile and individually packed, ready for being used.

Another pad of gauze that can be used for cases similar to the one with hip surgery, or similar to that unit, is shown by FIGS. 35, 36 and 37. In this case, a pad of gauze has one open surface 158 to absorb the blood and secretions. When the other sides of it 155, 157 are covered by a thin plastic layer to prevent from contaminating the sides of the balloon.

The pressure dressing system of combinations of balloons and wraps may also be used in the application of certain drugs in certain circumstances, such as psoriasis, or some infections and inflammations of skin, where pressure may help the penetration of medication much more deeply and effectively inside the affected area, and the body in certain cases (such as Nitro-Bid ointments, corticosteroid, hormones, etc.) And also in cases when there is hematoma in the limbs, in that early pressure may prevent further expansion. Then such units may be very useful (hemophiliacs). Especially when they can provide both cold and pressure simultaneously, or even heat.

The balloons can be either permanently sealed or have a port for inflation by different methods, such as syringes or bulbs, etc. This port is to have a valve that will open when the syringe or inflation bulbs are connected to it. The pressure inside the balloons can be monitored simply by having a smaller balloon connected to the side of the inflation port by a small tube of their own. Or, the smaller balloon will be part of the inflation system and in part of the inflation port as shown in FIGS. 22 and 23, and the equalization of the pressure inside the main balloon and the smaller balloon will give a reasonable idea about the magnitude of the pressure. The measurement of the pressure inside the balloon can be done by a pressure gauge or monitor of various methods connected to the balloon. An alarm may also be used in certain cases to allow the medical staff to notice the change in the pressure inside the balloon.

In order to collect and drain the blood and the secretions from the site of operation, a drain may be needed to be placed. A unit will be made to have a curved line or area in the middle of its surface so that the drain can be placed under the balloon and be protected by a piece of matching hard plastic that will stay over the drain and under the balloon preventing pressing on the drain. A piece of hydrophilic material in the shape of a tape or rope can be used to stand over the cut area to absorb the secretions. The end of this piece will be carried to an open area to allow visualization of these secretions.

As mentioned earlier, the use of these balloons will give the chance of using different levels of heat in the area without the need to remove the dressing. This can be accomplished by circulating warm or cold water by a small electric pump that will circulate the water with a desired temperature through the balloons. The water will go through one port inside the balloon, and then come from the other side to go inside the pump system for adjusting its temperature. Naturally, the balloon will be made from temperature-resistant material, which is available at this stage of progress of petrochemical science. During this period, when the water is being circulated, either the air would be emptied and the water would replace the air for inflation of the balloon, or a different compartment in the balloon may be used for this purpose, or different balloons designed for this purpose will be next to each other to allow this goal to be achieved. This will provide a unit in which some balloons or parts of a balloon will maintain the pressure while the other parts allow circulation of the water. These options will give freedom of choice in each case, and, based on these needs, different units will be made. For example, the use of heat after knee surgery may be more comforting and favorable for a patient, whereas for burned areas, the circulation of iced or cold water will be a better choice in acute cases.

In order to secure the shape of the unit, it is possible, when necessary, to include layers of pre-shaped plastic or metal sheets to give the desired shape. The shapes have to match the need in each side and case. For example, in the case of knee surgery, the pieces will have a shape that will match the shape of the sides of the knee. And in the groin cases, a slightly curved unit may serve the purpose better. In the case of the knee during the period when it needs to be immobilized, hard pieces will be used, and later a piece that has a joint or soft part can be chosen in the sides to allow the unit to be bent and to let the knee be bent. It is possible to combine these two into one unit—a lock to immobilize the knee, and to be released for motion.

In general, these hard pieces will be placed either inside or outside of the support system and under the straps or wraps so that they hold the unit in place and be effective.

Naturally, the size of the units will be different to match different size patients. The balloons can be small connected pieces with a narrow connecting part in between so that the rest of the balloon can be taped over itself in those areas to make the total length of the piece smaller.

OTHER ADVANTAGES OF THESE UNITS

First, I believe that there are significant advantages of using this method, and the new techniques that are introduced herein. First, it will decrease the time of dressing from minutes to seconds. Thus, the job of dressing can be done faster. The need for preparation of the area for heavy taping and application of the sticky material TinCoBen, and cutting the tapes and applying them, will be eliminated or reduced. In many cases, these units can be used with lots of ease. Naturally, the area should be clean, and application of these units needs to be done with attention and precision. But it would not take much time and there are only a few straps to be closed for the unit to be functional.

Second, the exchange does not require many adhesive tapes to be removed when some models may not have adhesive surfaces. The others will have a narrow rim of adhesive around them (which can be in interrupted areas to cut the total area of the adhesive film smaller), so that the pain of removing the adhesive tapes will be much less.

Third, the pressure generated by the balloons is controllable and adjustable as many times as anyone wants to do.

Fourth, the change of the unit does not, in some models, require dismantling the whole unit; therefore, it will be simpler. The models with windows in the center will allow the exchange of dressing to be done much easier. Inspection would be possible and even wiping the wound and heat application will be possible.

Fifth, the application of pressure in certain cases, such as the unit for herniorrhaphy, has its advantage of allowing early mobilization of the patient, since supporting the newly created wall against intra-abdominal pressure is possible by the balloon and the wrap around it. This will give reasonable assurance to the patient that the incision will not be under as significant stress as would be the case if the balloon pressure were not present. I believe the peace of mind of these patients (based on logic and reasoning) is very valuable and important. The same thing is very true after the use of angioplasty and cardiac catheterization. I personally have had many patients who, even after many days of catheterization, were still worried that their activity and motion could make their punctured vessel in the groin open and bleed. We doctors use many millions of dollars worth of tranquilizers to put patients' minds at ease, and naturally it would be many times better if the assurance and peace of mind can be done without the use of medication and by a simple way such as mentioned herein.

Sixth, it is also important to notice that in many cases these units will replace the use of adhesive tapes and heavy utilization of gauze. Therefore, the expense will not be adding something over the present method, but replacing them.

Seventh, the pressure is not position- and gravity-dependent, such as in the use of sandbags, and so it will give more freedom to patients.

Eighth, the construction of the windows will allow the inspection and cleaning of the wound to be done much more easily so that the chance of complications will be much less.

EXPLANATION OF SOME UNIQUE UNITS

Pressure bandages: These are mentioned in the text as prototype and will be easily used to prevent bleeding after venipuncture, small surgeries on skin lacerations, etc. Their size will vary, and larger units can be made with the same shape. The balloons in small units will be pre-inflated, but in larger units will be made with balloons that can be inflated by standard syringes to allow the size of the balloon to be in a desired range. They can have circular or oval shapes. They will be individually wrapped and can be used easily. Some may be premedicated.

Units for subclavian line removals etc.: These units are basically similar to the one mentioned above, except they will be larger and shaped like a triangle to fit the place they are used. Their balloon will be pre-inflated although some models will be made with balloons that need to be inflated and can be inflated by standard syringes to allow the size of the balloon to be in a desired range. The system to keep them in place will be adhesive taping or straps. They will be individually wrapped, and can be used easily.

Units for prevention of bleeding after cuts: These units will be similar to the units mentioned in the previous two headings, and they will be combinations of those made in different sizes, mostly to have the shape of a rectangle or an oval shape to be held in place with adhesive covered bands or straps and wraps to be used to prevent bleeding in emergencies such as accidents, etc., until more appropriate care can be given by professionals. Their balloons will be pre-inflated although some models will be made with balloons that need to be inflated and can be inflated by standard syringes to allow the size of the balloon to be in a desired range.

The unit after herniorrhaphy: A distinct model will be a unit to be used after herniorrhaphy. This unit will have a shape similar to a triangle to cover the area where the hernia has been operated, and to cover the weak areas of the abdominal and inguinal areas after such surgeries, in order to counteract the pressure from the inside of the abdomen and to support the newly made abdominal wall at the site of surgery. The unit is shown in FIGS. 15 and 16. The main piece 27 will stay over the operated area and will be held in place with the use of strap 28-29-30-32, that goes around the waist and is tightened by piece 31-33. Also, the strap 35-39-36 will be tightened by piece 37-38. The balloon 7 will be inflated by inflation port of 34. The port has a valve that will close when the inflation instrument, such as a standard syringe, is removed. The straps may have a part of elastic among their construction. The size and pressure inside the balloon can be changed with inflation. The surface of this balloon may accept the gauze that have the adhesive film on it.

This unit may also have a window similar to the one shown in FIGS. 33 and 34 for inspection and exchange of the pads of gauze as mentioned. In FIG. 33, the outside rim 150 is shown. The cover 151 is hinged with no 152 and can be held in place by snap 153. In this revolutionary way, the window will be opened (FIG. 34), and the previous gauze will be removed. After inspection and cleaning, the new dressing will be inserted. After the new pad has been placed, it will be held in place by closing the cover and the use of the hard support system. The surface of the cover over the gauze may be covered by a balloon to press the gauze against the wound to give reasonable support. This unit has many advantages and will be quite useful when a patient is going to be discharged and has to change the dressing himself.

A unit for using after cholecystectomies: This unit will be similar to the one mentioned for herniorrhaphy, except the unit will be somewhat bigger and have the wrap go around the upper abdomen, lower chest area, with straps to go from front to back, and over the shoulder area on the right side to hold the unit in place. And here a balloon or combinations of the balloons can be used to give the same kind of useful techniques mentioned above. Naturally, the units with windows can be used too.

A unit for using after appendectomies: This unit will be similar to the one mentioned for cholecystectomies and herniorrhaphies, and have the wrap go around the lower abdomen area, and straps may be needed to go from front to back, and over the shoulder on the right side to hold the unit in place. Naturally, the units with windows can be used too.

A unit that can be used after abdominal surgeries: This will be basically similar to the one mentioned above, that is used after a hernia operation. And here a balloon or combinations of the balloons can be used to give the same kind of useful techniques after many other abdominal wall or intra-abdominal surgeries. I believe that after any of these kinds of surgeries, it would be better for the patient if the walls of the abdomen could be supported, thus avoiding intra-abdominal pressure from being applied to the wall and weakening the newly made wall. Especially in certain conditions, such as obesity and severe coughing, the need is much more obvious, and the extra intra-abdominal pressure is much more likely to cause some degree of weakness in the newly made wall after abdominal surgery that may not be detectable first, but may show up sometimes later in life. This can be easily protected by the units I have introduced. Here, the wraps that support the balloons are wide and strong, and easily adjustable by the use of Velcro TM systems and belts at the end sides. And the special dressing will allow the patient to be mobilized faster to prevent complications that happen due to immobility. These wraps may have a special pocket to allow the suction part of the drainage system to be positioned.

The units for the incisions in the center of the abdomen may have a similar shape to that shown in FIGS. 17, 18, 20 and 21 for the units for hip operations, except the wraps and straps will be positioned to keep the balloon in the center of the abdomen. The balloons will have a matching concave curved surface to match the convex shape of the abdominal wall.

Here, the units that have openings in the center will allow the sensitivity of the site of incision to be avoided, making a nice method that can be used with much comfort. This is important, since after the operation, the site of incisions may stay sensitive for a long time, even months. And if the situation requires pressure to be applied to the site of the operation by avoiding the cut area, then this unit will show its unique ability.

A unit to be used after mastectomies: This unit will have a rather rectangular shape with mild concave curvature in its inner surface, and can be held in place by straps or wraps that go around the chest. The unit may have one or multiple balloons. It may also have a combination of balloons that will leave a space in the center of the balloons free for the drain to be positioned. The unit may also have a window for easy inspection.

I would like to mention here an important point: The window will also allow a model of gauze to be used with an empty curved line or area in its center to match and stand over the incision and allow the draining tube to be easily placed for drainage. Overall, these will give better chance of care of the operated area with use of less adhesive tape and less bleeding.

Thoracic surgeries will also be one of the many forms of surgeries with which these units can be used with ease. Here, the model that has a double balloon has its own unique advantage of allowing the sides of the wound and the cut area to be pressed while the central cut will be spared.

The model with an open center will also have its unique role in the case of thoracic surgery to hold the structure, but avoid the incision line, and allowing inspection, etc. For these purposes, units similar to the one shown in FIGS. 17, 18, 20 and 21 for hip operations, can be used, except the wraps and straps will be positioned to keep the balloon in the center of the chest or the side, as they are needed.

For operations in the lungs, and cases where the ribs are to be separated, similar units will be made with the exception that the balloons and the shape of the unit will be changed to match the size and shape of operation and incision site. For example, when the ribs are opened, the balloons would have shape and a surface curve to stay along the ribs and the open centers to match the site of the incision.

Use of this unit after coronary angioplasty: This is a circumstance where use of this balloon can be very helpful in prevention of hematoma and bleeding after cardiac catheterization and coronary angioplasty. For this reason, I have originally applied for the two previous inventions mentioned at the beginning.

What I have introduced before, and I now improve, is a wrap made from plastic that goes around the upper thigh and is kept there securely. On the top of this wrap there will be a plastic molding or cradle that matches the shape of the body of the arterial and venous sheaths and allows them to be positioned and kept there securely and easily, and a smaller wrap to go over the body of those sheaths located on the cradle to keep them securely in place. This same unit is made somewhat more effective here by adding the balloon or balloons to stay under the wrap in the upper thigh area, as shown, in the groin over the large vessels in that area so that the pressure applied by the balloons and supported by the soft, strong, non-stretchable wraps will match and may be slightly exceeded to overcome the pressure inside the pressure inside the vessel, both of which can be measured easily. (One is the pressure inside the artery, and the other one is the pressure inside the balloon that can be also connected to a pressure device. With use of a three-way stopcock, it can be connected to the same monitor that measures the pressure of the artery, which is really easy to be done and it can measure it every time we want.)

I believe this unit will be exceptionally good for such problems and will diminish the size and amount of bleeding and hematomas significantly.

A unit to be used in wrist after removal of arterial line in the wrist: A smaller balloon covered by a layer of gauze can be wrapped on the site of removal of an arterial line in the wrist and be tightened by a Velcro TM system to prevent bleeding.

The other surgeries I would like to indicate that although I did not mention the name of all kinds of surgeries which these units will be useful, it is reasonable to believe that with modifications of these basic ideas, units can be made to be used in many cases after almost all surgeries.

The units for orthopedic uses: This basic technique can be also useful in the cases of casting broken limbs. A multiple lumen balloon can be used (shown in FIGS. 38, 39, 40 and 41) to cover the skin over the soft dressing. This will allow control of pressure under the cast, which I believe will be very useful when there is a need to decrease the pressure applied by the cast. This technique would be unique in allowing it to happen so that the skin and the muscles can be perfused and tension diminished when one group of the balloons is deflated, and another adjacent group is kept inflated to prevent disfiguring of the whole unit. I also want to present models where the balloons are covered with the casts except in cases that have a line of cut in front with walls and a piece in the back with hinges. Then, after the cast is applied and has taken its shape, the cast will be cut along these lines to allow the whole cast to be opened, like opening the shell of a peanut along the line of symmetry, in order to be able to check the area, eliminating the need for removing the whole cast and applying a new one. Two plastic pieces, one in the front with a place for locking and one in the back with hinges, will allow this to happen.

What is claimed is:

1. A dressing for application to an area of the body containing a wound, said dressing comprising absorbent material for placement on such an area, balloon means disposed over said absorbent material, and a support system for holding said balloon means over said absorbent material so that said balloon means can apply pressure to such an area, characterized in that said support system comprises a cover that is relatively more rigid than said balloon means and that is disposed over said balloon means, portions of said cover and said balloon means comprise means defining an open space that extends through said cover and said balloon means to the wound thereby providing access to the wound via said cover and said balloon means, in which said means defining an open space that extends through said cover and said balloon means to the wound comprises an opening that passes through a central region of said cover and an opening that passes through a central region of said balloon means, in which said absorbent material comprises a unit of absorbent material that occupies said open space and is removable from said open space via said opening so that the unit can be replaced without removing said balloon means and said support system, and including a door for opening and closing the opening in said cover.

2. A dressing as set forth in claim 1 in which said balloon means extends endlessly around the opening that passes through its central region.

3. A dressing as set forth in claim 1 in which said unit of absorbent material comprises medicine carried by the absorbent material thereof.

4. A dressing as set forth in claim 1 further including a further balloon means disposed between said door and said unit of absorbent material for controlling pressure applied to said unit of absorbent material.

5. A dressing as set forth in claim 4 wherein said further balloon means is clear.

6. A dressing as set forth in claim 5 wherein said door is clear.

7. A dressing as set forth in claim 1 wherein said door is clear.

8. A dressing as set forth in claim 1 wherein said unit of absorbent material comprises a central gauze pad surrounded by a plastic wall to prevent secretions absorbed by the gauze pad from diffusing and reaching said balloon means.

* * * * *